United States Patent [19]

Sommerkamp

[11] Patent Number: 5,197,966
[45] Date of Patent: Mar. 30, 1993

[54] RADIODORSAL BUTTRESS BLADE PLATE IMPLANT FOR REPAIRING DISTAL RADIUS FRACTURES

[76] Inventor: T. Greg Sommerkamp, 273 Springside Dr., Crestview Hills, Ky. 41017

[21] Appl. No.: 887,735

[22] Filed: May 22, 1992

[51] Int. Cl.⁵ .................. A61B 17/56; A61B 17/58
[52] U.S. Cl. ............................. 606/69; 606/70
[58] Field of Search .................. 606/60, 69-75, 606/53

[56] References Cited

U.S. PATENT DOCUMENTS

| | | | |
|---|---|---|---|
| 4,565,193 | 1/1986 | Sfreli | 606/69 |
| 4,651,724 | 3/1987 | Berentey et al. | 606/69 |
| 5,006,120 | 4/1991 | Carter | 606/69 |
| 5,015,248 | 5/1991 | Burnstein et al. | 606/69 X |

*Primary Examiner*—Ronald Frinks
*Attorney, Agent, or Firm*—Frost & Jacobs

[57] ABSTRACT

A radiodorsal buttress blade plate assembly includes blades that are rigidly secured to a side plate and are arranged in an offset position to facilitate placement in close proximity to the cortical bone surface.

12 Claims, 2 Drawing Sheets

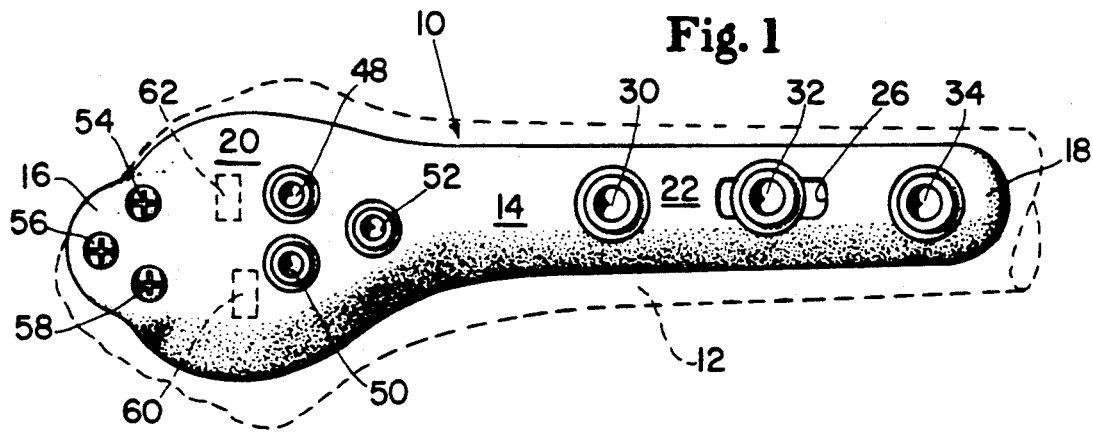
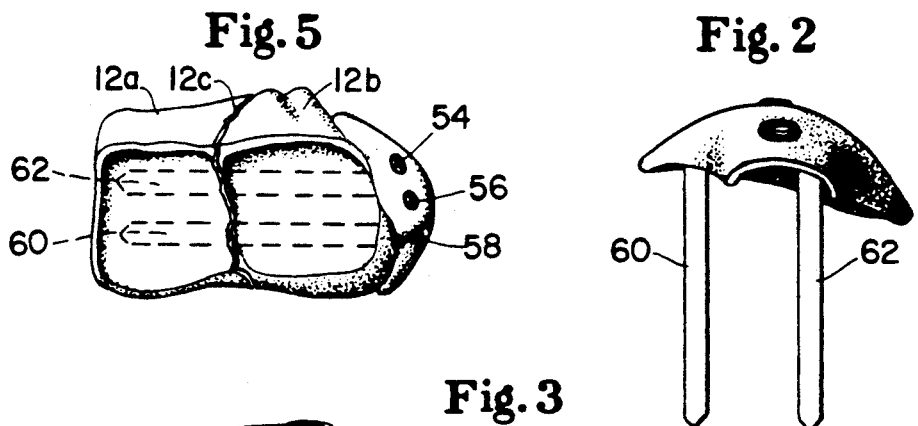
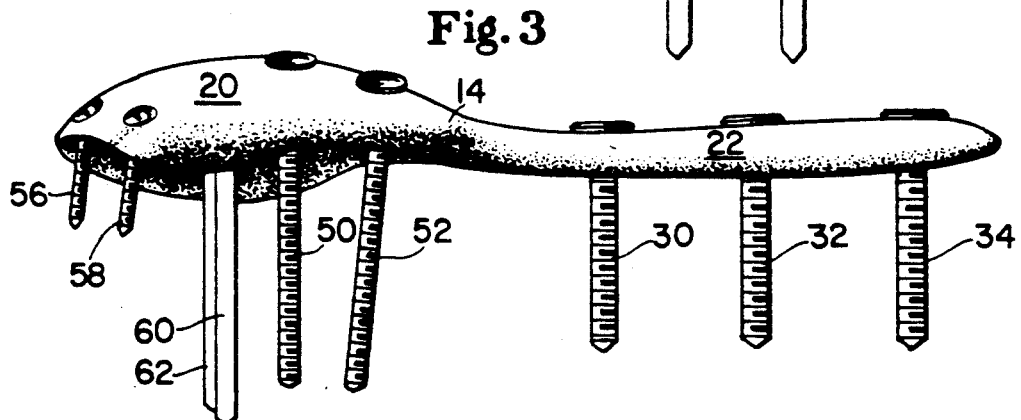
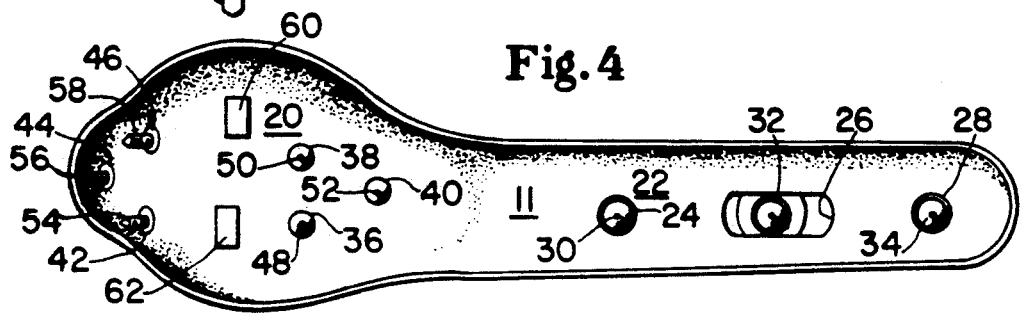

RADIODORSAL BUTTRESS BLADE PLATE IMPLANT FOR REPAIRING DISTAL RADIUS FRACTURES

TECHNICAL FIELD

The present invention relates generally to fixation devices for fractured bones and is particularly directed to an implantable side plate for immobilizing fractured bones with a combined buttress and blade plate. The invention will be specifically disclosed in connection with a buttress blade plate specifically configured to the peculiar anatomical contours of the radiodorsal aspect of the distal radius.

BACKGROUND OF THE INVENTION

One of the most common types of bone fractures that occurs in humans is a fracture of the distal radius. In repairing these fractures, it is desirable to set the components of the fractured bone in a proper alignment, and to thereafter immobilize the bone to prevent relative movement between the fractured components during a period of healing. While it is desirable to immobilize relative movement between the fractured bone components during the bone healing period, it also is highly desirable to maintain, and indeed to promote, movement of the adjacent wrist joint during this same period. In order to achieve these seemingly inconsistent objectives, several types of fixation devices have been developed.

The prior art fixation devices for immobilizing the fractured components of the radius bone have been of two general types, external and internal. Although external fixation devices have been found to be effective in certain instances for specific kinds of fractures, they are aesthetically objectional to many people, and are prone to numerous complications, such as infection at the pin sites.

One prior art internal fixation device for immobilizing distal radius fracture components is described in U.S. Pat. No. 5,006,120 to Carter. This device uses a side plate that is secured to the dorsal portion of the radius by a plurality of screws. The Carter plate supports a plurality of attachable U-shaped blades at one of its longitudinal ends. These U-shaped blades are placed in a correspondingly U-shaped groove cut through the fractured components, and the blades are thereafter threadably secured to the plate.

While the internal fixation device of the above-referenced patent offers a number of advantages, it also is incumbered with a number of disadvantages. For example, the Carter plate is generally planar, and its use is limited to the dorsal portion of the distal radius bone. However, such a position is inappropriate for the more commonly oriented fractures which extend in a direction transverse to that plate. In addition, the U-shaped blades disclosed in this patent, which are attachably secured to the plate, are capable of movement relative thereto, especially when substantial stress is applied to that area of the body. Any such relative movement between the blades and the side plate, of course, permits corresponding relative movement between the fractured bone components. Moreover, exercise of the wrist, which most desirably and advantageously produces synovial fluid and lubricates the cartilage during the bone healing process, produces substantial stress on a distal radius bone. For example, gentle movement of the wrist can produce pressures in the range of 20 pounds per square inch, while squeezing with the hand to make a fist can produce pressures in the order of 120 pounds per square inch.

It is also highly advantageous, when securing fractured bone segments in their anatomically correct positions, to attach the fixation apparatus to the cortical portion of the bone. Unfortunately, this cortical portion is relatively thin, in the order of 2-3 mm in thickness, and the positioning and securing of a fixation apparatus into the relatively thin layer of cortical bone or into the mineral dense juxta-articular cancellous bone is quite difficult.

SUMMARY OF THE INVENTION

Accordingly, it is a primary object of the present invention to provide an implantable fixation apparatus for immovably securing fractured bone segments of the distal radius wherein the side plate is rigidly connected to one or more blades.

Another object of the present invention is to provide an implantable fixation apparatus for immovably securing fractured bone segments of the distal radius wherein one or more blades extend generally perpendicularly through a "die punch" fracture line in the distal radius, i.e., through a fracture line extending between the dorsal and volar surfaces.

It is another object of the invention to provide an implantable fixation apparatus for immovably securing fractured bone segments of the distal radius where blades, are provided that are solidly secured in subchondral or juxta-articular cancellous bone material.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved implantable buttress blade plate assembly for repairing a distal radius fractures is provided. The buttress blade plate assembly includes an elongated side plate extending in a first direction between first and second longitudinal ends. The side plate has an abutment surface that is configured to match the anatomical contours of the distal radiodorsal portion of the radius bone. The side plate also has a first enlarged portion proximal to one of its longitudinal ends in which the side plate extends in a second direction perpendicular to the first direction for a distance greater than the corresponding extension in the second direction of a second adjacent portion of the side plate. A plurality of openings extend through the side plate. Each of the openings is spaced from each other in the first direction and is dimensioned and configured to accommodate a screw for securing the side plate to the radius bone. A pair of elongated blades is rigidly secured to and extends outwardly from the abutment surface at the enlarged portion of the side plate. Each of the blades extends in a third direction generally perpendicular to both the first and second directions, with the blades being spaced from each other in the both the first and second directions.

In a more specific form of the invention, the blades are arranged such that a line connecting the respective center lines of the blades intersects the longitudinal axis of the side plate at an angle ranging from approximately 4 to 16 degrees. This spacial relationship advantageously allows blades to be secured in the mineral dense juxta-articular cancellous portion of the bone. The center lines more preferably intersects the longitudinal axis of the side plate at an angle of approximately 7 to 11 degrees, and most preferably at approximately 7 degrees.

The implantable buttress blade plate assembly of the invention preferably includes at least three openings in the side that are aligned in the first direction, with at least one of the openings being a slot extending in the first direction. In addition, the invention preferably includes a first series of openings on the proximal side of the blades and a second series of openings disposed on the distal side of the blades. Screws extend through these openings to secure the side plate to the radius bone.

In accordance with another aspect of the invention, the side plate and the blades have a unibody construction to increase rigidity.

According to another aspect of the invention, at least one of the blades is on each side of a center line of the side plate extending in the first direction.

Still other objects of the present invention will become apparent to those skilled in this art from the following description wherein there is shown and described a preferred embodiment of this invention, simply by way of illustration, of one of the best modes contemplated for carrying out the invention. As will be realized, the invention is capable of other different embodiments, and its several details are capable of modification in various, obvious aspects all without departing from the invention. Accordingly, the drawing and descriptions will be regarded as illustrative in nature and not as restrictive.

BRIEF DESCRIPTION OF THE DRAWING

The accompanying drawing incorporated in and forming a. part of the specification illustrates several aspects of the present invention, and together with the description serves to explain the principles of the invention. In the drawing:

FIG. 1 is a top plan view of an implantable buttress blade plate assembly constructed in accordance with the principles of the present invention as it would be seen in abutting relationship with the radiodorsal surface of the distal radius bone;

FIG. 2 is an end view of the enlarged longitudinal end of the buttress blade plate assembly of FIG. 1;

FIG. 3 is a side elevational view of the buttress blade plate assembly of FIG. 1;

FIG. 4 is a bottom plan of the buttress blade plate assembly of FIG. 1 showing the abutment surface;

FIG. 5 is an inferior view of the distal radius bone showing the abutment surface of the buttress blade plate assembly of FIG. 1 in contacting relationship with the bone's radiodorsal surface;

Figure 6:
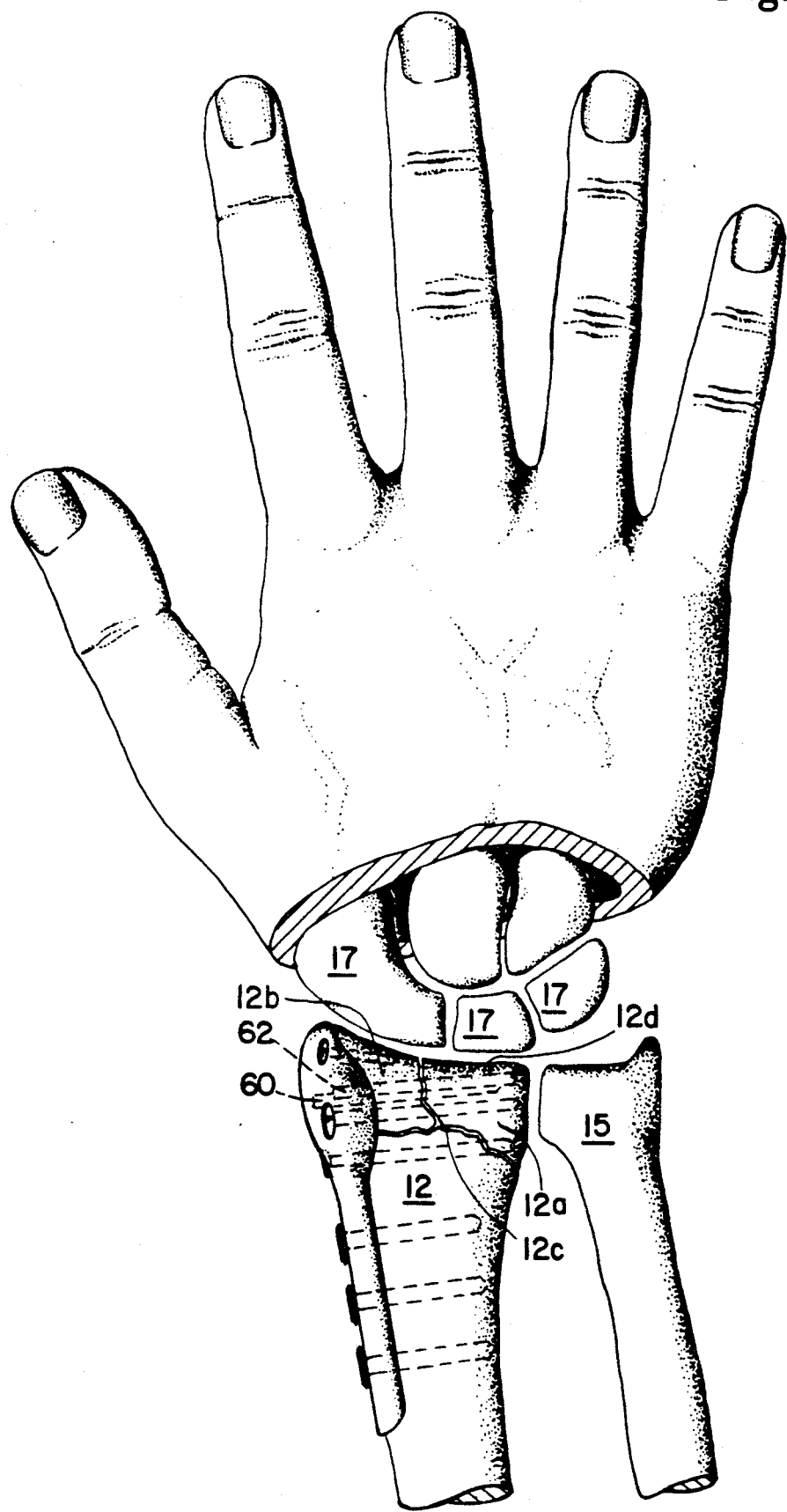
FIG. 6 is a posterior view of a human hand and wrist showing the buttress blade plate assembly of FIG. 1 securing fragmented components of a fractured distal radius bone in correct anatomical alignment.

Reference will now be made in detail to the present preferred embodiment of the invention, an example of which is illustrated in the accompanying drawings.

DETAILED DESCRIPTION OF THE PREFERRED EMBODIMENT

Referring now to the drawings, FIG. 1 depicts the top, exterior surface of an implantable buttress blade plate assembly, generally designated by the numeral 10, that is constructed in accordance with the principles of the present invention. The illustration of FIG. 1 shows the blade plate assembly 10 secured to the radiodorsal surface of a distal radius bone 12, which bone 12 is depicted in phantom lines only. The bone is contacted by an abutment surface 11 of blade plate assembly, which abutment surface 11 is most clearly illustrated in FIG. 4. As perhaps best realized from jointly viewing FIGS. 2 and 3, the abutment surface 11 is contoured so as to match the anatomical contour of the radiodorsal surface of the distal radius bone 12 with which it is in contact.

The blade plate assembly 10, which is shown in end and side views in FIGS. 2–3, includes an elongated side plate 14 extending in a first direction (extending generally horizontally across the drawing illustration of FIGS. 1, 3 and 4) between its first and second longitudinal ends 16 and 18, respectively. The side plate 14 has an enlarged portion 20 proximal to the first end 16. This enlarged portion 20 extends in a second perpendicular direction (generally vertical on the drawing sheet illustration of FIGS. 1 and 4) for a distance that is greater than the corresponding extension of the adjacent narrow section 22 of the side plate 14 in this second direction.

The narrow section 22 of the side plate 10 includes a plurality of longitudinally aligned and spaced openings 24, 26 and 28 (the openings 24 and 28 are obscured by the screw heads in FIG. 1, see FIG. 4), each of which extends through the side plate 14 and is respectively dimensioned and configured to receive the shaft of a screw 30, 32 or 34 used to secure the side plate 14 to the bone 12. The openings 24 and 26 are generally circular, and dimensioned slightly larger than the shafts of the screws 30, 32 and 34, but substantially smaller than the screw heads. The opening 26, however, has a slot-shaped configuration which allows the surgeon to partially insert the screw 32 and to thereafter longitudinally adjust the relative position of the side plate 14 relative to the bone 12. In the preferred embodiment, the screws 30, 32 and 34 are approximately 3.5 mm in diameter. The length of these screws 30, 32, and 34 is based on the patient's anatomy.

The enlarged portion 16 of the side plate 14 also includes a plurality of openings for receiving screws to secure the side plate to the bone 12. These openings are arranged in two identifiable groupings, a first more proximally located triangular series of openings 36, 38 and 40 (see FIG. 4) and a second more distally located series of openings 42, 44 and 46. The first series of openings 36, 38 and 40 receives screws 48, 50 and 52 and the second series of openings 42, 44 and 46 receives screws 54, 56 and 58. The screws 48, 50 and 52 are preferably 2.7 mm in diameter while the screws 54, 56 and 58 preferably have a diameter of approximately 2.0 mm.

Longitudinally interposed between the first and second series of openings in the enlarged portion 16 of the side plate 14 are two elongated blades 60 and 62. The blades 60 and 62 are rigidly secured to the side plate 14, preferably in a unitary construction, and extend outwardly from the abutment surface 11 (depicted in FIG. 4) of the side plate 14 in a third direction that is substantially perpendicular to the first and second directions. As shown in the FIGS. 1 and 4, one of the blade plates 60 or 62 is on each side of the longitudinal center line of the side plate 14. Advantageously, and in accordance with one of the principle aspects of the invention, the blade plates 60 and 62 are positioned with the top or dorsal blade 62 slightly more distal than the bottom or volar blade 60. This arrangement is such that a line connecting the centerlines of the blades 60 and 62 would intersect the longitudinal axis of the side plate 14 at an angle between approximately 4 to 16 degrees, and more preferably between 7 to 11 degrees. In the preferred embodiment this angle is optimally selected as 7 degrees.

This relative positioning of the blades 60 and 62 gives the surgeon the unique capability of lagging the radial styloid fragment 12a to the medial complex 12b or "die punch" fragment with the blades and the screws 48, 50 and 52. In addition, the radiodorsal positioning of the side plate 14 enables the surgeon to utilize the "counter buttress" effect of the intact ulnar head.

As those skilled in the art will appreciate, the relative angular positioning of the blades 60 and 62 are matched to the volar profile angle of the distal radius bone. By matching the profile in this way, positioning of the blades in the mineral dense juxta-articular cancellous bone is greatly facilitated.

In the preferred embodiment, the blades 60 and 62 have cross-sectional dimensions of approximately 2.7 by 1.2 mm, with a length that is selected to match the anatomy of the patient. Preferably, the blades are manufactured with a length sufficient to accommodate the larger anatomies, in the order of 35 mm, and are thereafter cut to accommodate smaller patients.

FIG. 5 depicts a fractured radius bone that is secured in proper alignment by the blade plate assembly of FIGS. 1-4. It can be seen from this drawing that the abutment surface 11 conforms to the radiodorsal surface of the distal radius bone 12 and that the blades 60 and 62 extend through the fracture 12c. The screws 54, 56 and 58 are removed from the illustration of FIG. 5 so as to avoid obscuring the view of the blades 60 and 62.

FIG. 6 shows the distal radius bone 12 in its relative position with respect to the ulna 15 and carpal bones 17, and shows how the radial styloid is lagged into alignment with the screws. As is apparent from FIG. 6, the blades 60 and 62 extend in to a position in close proximity to the juxta-articular surface 12d. It can also be seen that the screws 48, 50 and 52 extend into the fragmented bone component 12b. As indicated above, these screws 48, 50 and 52 can lag the bone segment 12b providing compression against bone component 12a.

In summary, numerous benefits have been described which result from employing the concepts of the invention. The blade plate assembly of the invention provides blades that are rigidly connected to a cooperating side plate, and allows the patient to exercise the wrist during the rehabilitation process for a fractured distal radius bone. The blade plate of the invention also offsets the blades by an angle that corresponds with the volar profile of the distal radius bone, a feature that facilitates secure placement of the blades in the juxta-articular cancellous bone.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

WHAT IS CLAIMED IS:

1. An implantable radiodorsal buttress blade plate assembly for repairing a distal radius fracture, comprising:
    a) an elongated side plate extending in a first direction between first and second longitudinal ends, said side plate having an abutment surface that is configured to match the anatomical contours of a distal radiodorsal portion of a radius bone, said side plate having a first enlarged portion proximal to one of its longitudinal ends in which the side plate extends in a second direction perpendicular to the first direction for a distance greater than the corresponding extension in the second direction of a second adjacent portion of the side plate;
    b) a plurality of openings extending through said side plate, each of said openings being spaced from each other in the first direction and being dimensioned and configured to accommodate a screw for securing the side plate to the radius bone;
    c) a pair of elongated blades rigidly secured to and extending outwardly from the abutment surface at the enlarged portion of the side plate, each of said blades extending in a third direction generally perpendicular to both the first and second directions, said blades being spaced from each other in the both the first and second directions.

2. An implantable buttress blade plate assembly as recited in claim 1 wherein the blades are arranged such that a line connecting the respective center lines of the blades intersects the longitudinal axis of the side plate at an angle ranging from approximately 4 to 16 degrees.

3. An implantable buttress blade plate assembly as recited in claim 2 wherein the line connecting the respective center lines intersects the longitudinal axis of the side plate at an angle of approximately 7 to 11 degrees.

4. An implantable buttress blade plate assembly as recited in claim 2 wherein the line connecting the respective center lines intersects the longitudinal axis of the side plate at an angle of approximately 7 degrees.

5. An implantable buttress blade plate assembly as recited in claim 2 wherein said plurality of openings extending through said side plate includes at least three openings aligned in the first direction.

6. An implantable buttress blade plate assembly as recited in claim 5 wherein said plurality of openings extending through said side plate includes a first series of openings on a proximal side of the blades and a second series of openings disposed on a distal side of the blades.

7. An implantable buttress blade plate assembly as recited in claim 6 further including a plurality of screws extending through the openings spaced in the first direction, said screws being operative to secure the side plate to the radius bone.

8. An implantable buttress blade plate assembly as recited in claim 7 wherein said plurality of screws has a diameter of approximately 3.5 mm.

9. An implantable buttress blade plate assembly as recited in claim 8 further including a first set of screws extending through the first proximal series of openings and a second set of screws extending through the second distal openings, each of the first set of screws having a diameter of approximately 2.7 mm and each of the second screws having a diameter of approximately 2.0 mm.

10. An implantable buttress blade plate assembly as recited in claim 2 wherein the side plate and the blades have a unibody construction.

11. An implantable buttress blade plate assembly as recited in claim 2 wherein at least one of the blades is on each side of a center line of the side plate extending in the first direction.

12. An implantable buttress blade plate assembly as recited in claim 5 wherein one of the three openings aligned in the first direction is a slot extending in the first direction.

* * * * *